(12) United States Patent
Henderson

(10) Patent No.: US 8,097,008 B2
(45) Date of Patent: Jan. 17, 2012

(54) LAPAROSCOPIC HERNIA MESH SPREADER

(75) Inventor: Eric Ross Henderson, Tampa, FL (US)

(73) Assignee: University of South Florida, Tampa, FL (US)

( * ) Notice: Subject to any disclaimer, the term of this patent is extended or adjusted under 35 U.S.C. 154(b) by 938 days.

(21) Appl. No.: 12/045,456

(22) Filed: Mar. 10, 2008

(65) Prior Publication Data

US 2008/0188874 A1    Aug. 7, 2008

Related U.S. Application Data

(63) Continuation of application No. PCT/US2006/034958, filed on Sep. 8, 2006.

(60) Provisional application No. 60/596,233, filed on Sep. 9, 2005.

(51) Int. Cl.
*A61B 17/00*    (2006.01)
*A61F 2/02*    (2006.01)

(52) U.S. Cl. ........................... 606/151; 606/213

(58) Field of Classification Search .............. 606/151, 606/213, 1, 108, 191, 192
See application file for complete search history.

(56) References Cited

U.S. PATENT DOCUMENTS

| | | | |
|---|---|---|---|
| 5,203,864 A | 4/1993 | Phillips | |
| 5,383,477 A | 1/1995 | DeMatteis | |
| 5,464,403 A | 11/1995 | Kieturakis et al. | |
| 5,862,975 A | 1/1999 | Green et al. | |
| 6,280,464 B1 | 8/2001 | Hayashi | |
| 2002/0117534 A1 | 8/2002 | Green et al. | |
| 2004/0173659 A1 | 9/2004 | Green et al. | |
| 2005/0177180 A1* | 8/2005 | Kaganov et al. | 606/151 |

FOREIGN PATENT DOCUMENTS

EP    0541987 A1    5/1993

* cited by examiner

*Primary Examiner* — Vy Q Bui
(74) *Attorney, Agent, or Firm* — Michele L. Lawson; Smith & Hopen, P.A.

(57) ABSTRACT

An apparatus is provided for the laparoscopic deployment and positioning of surgical materials, such as mesh. The mesh is applied by at least one extension arm which radiates from a central shaft. Alternate embodiments employ simultaneously and/or individually extended rigid arms, and simultaneously deployed resilient arms. Various methods are also disclosed for attaching the mesh to the abdominal wall once it is deployed by the extension arms. Illustrative attaching methods include staples, low viscosity adhesives, and electrocauterization.

30 Claims, 7 Drawing Sheets

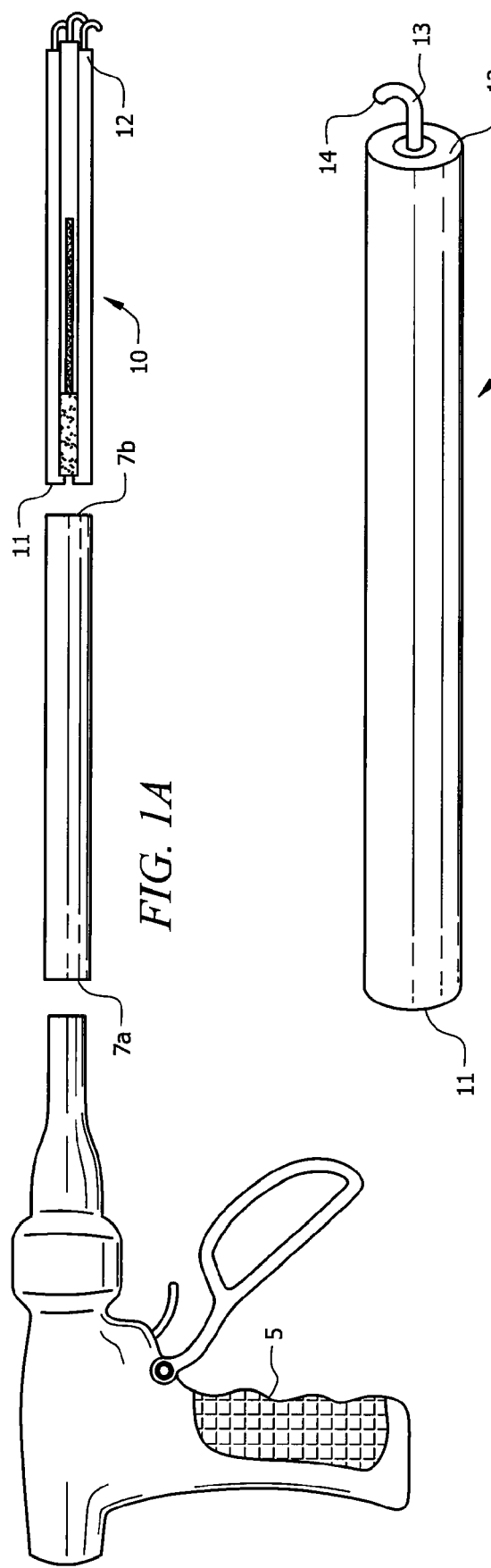

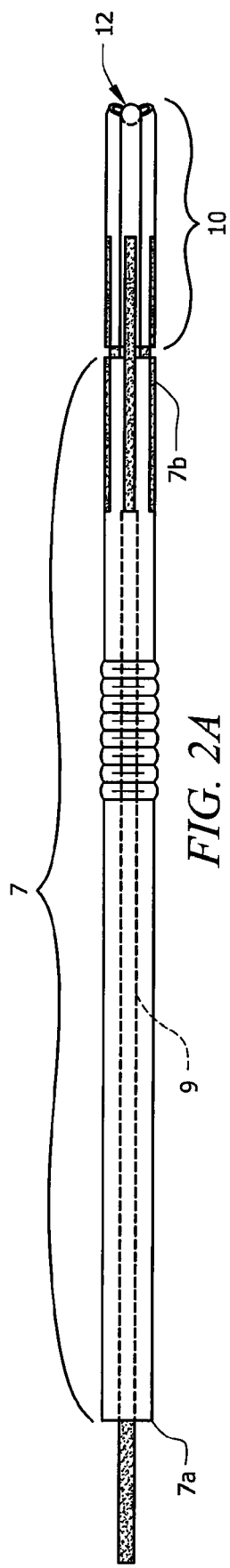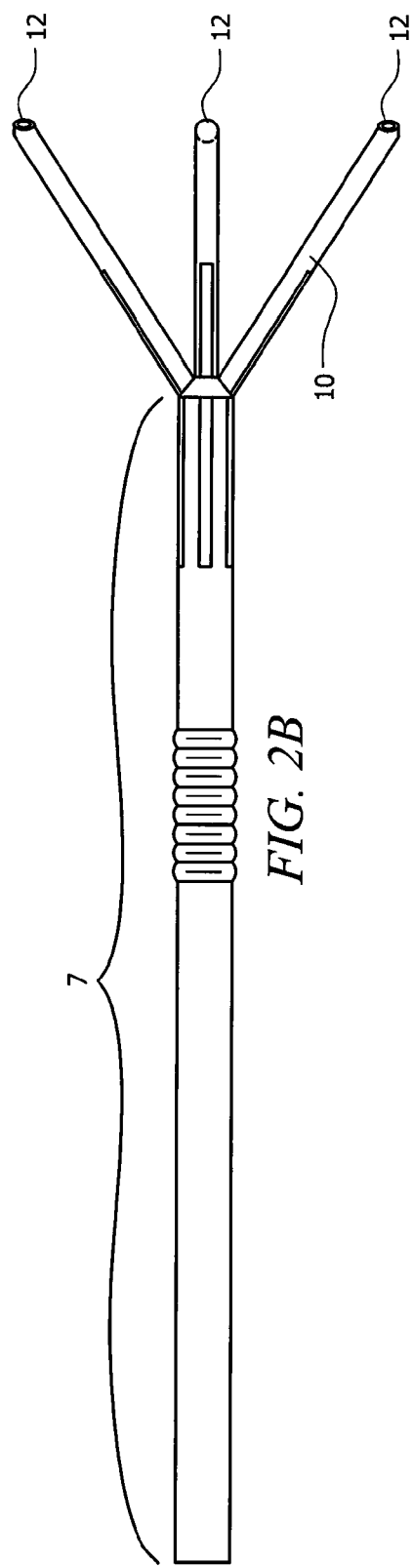
FIG. 2A
FIG. 2B

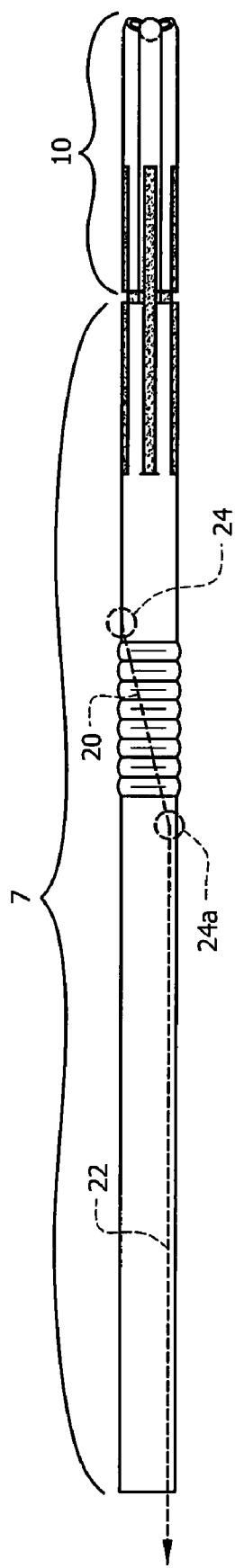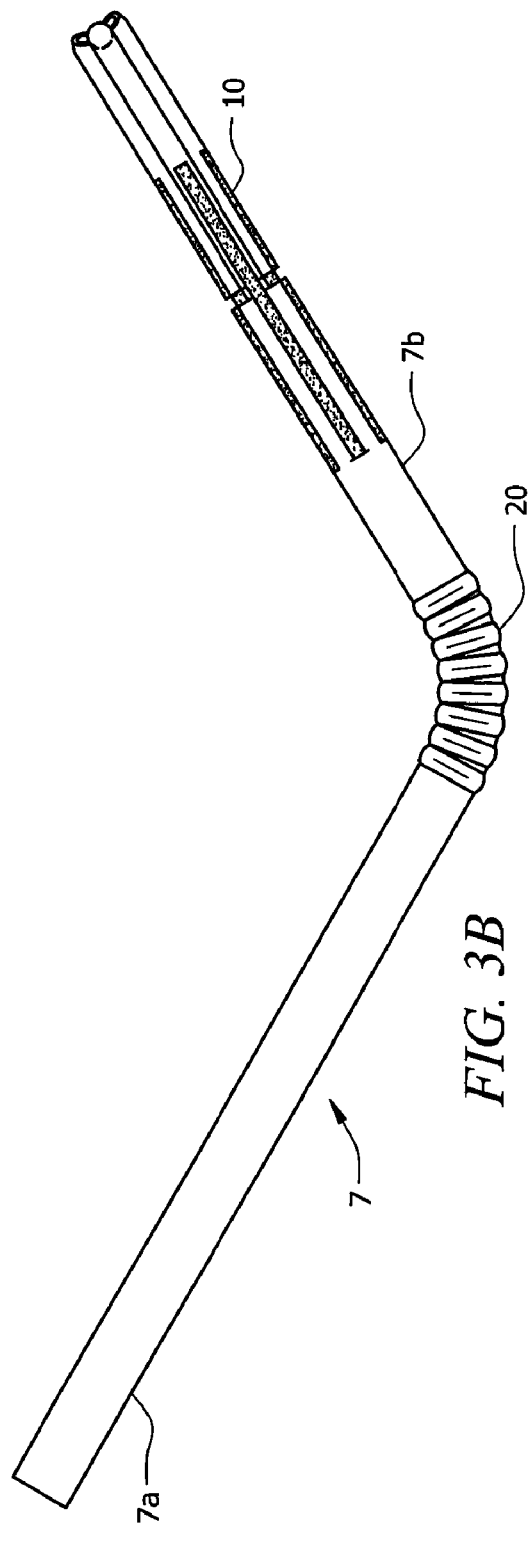
FIG. 3A
FIG. 3B

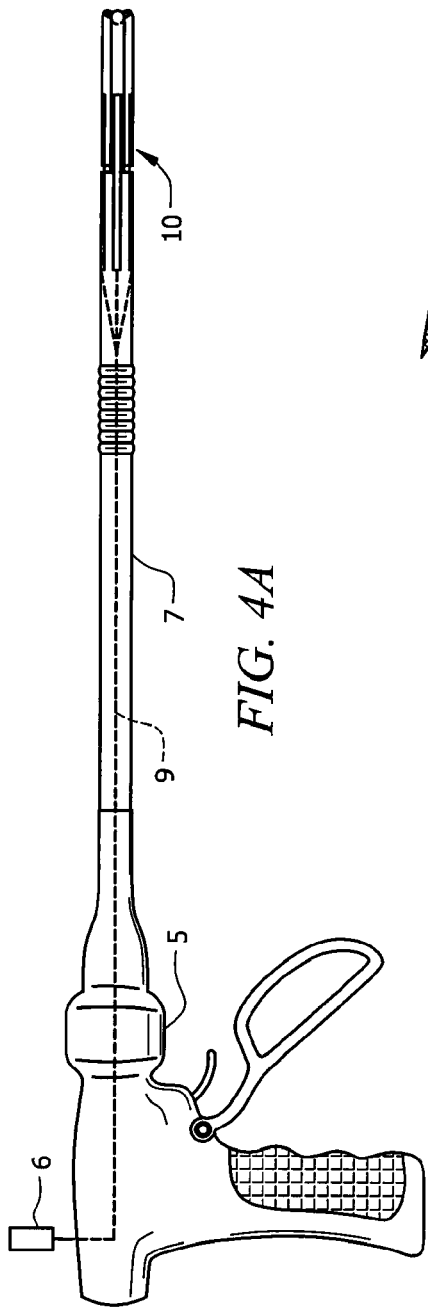
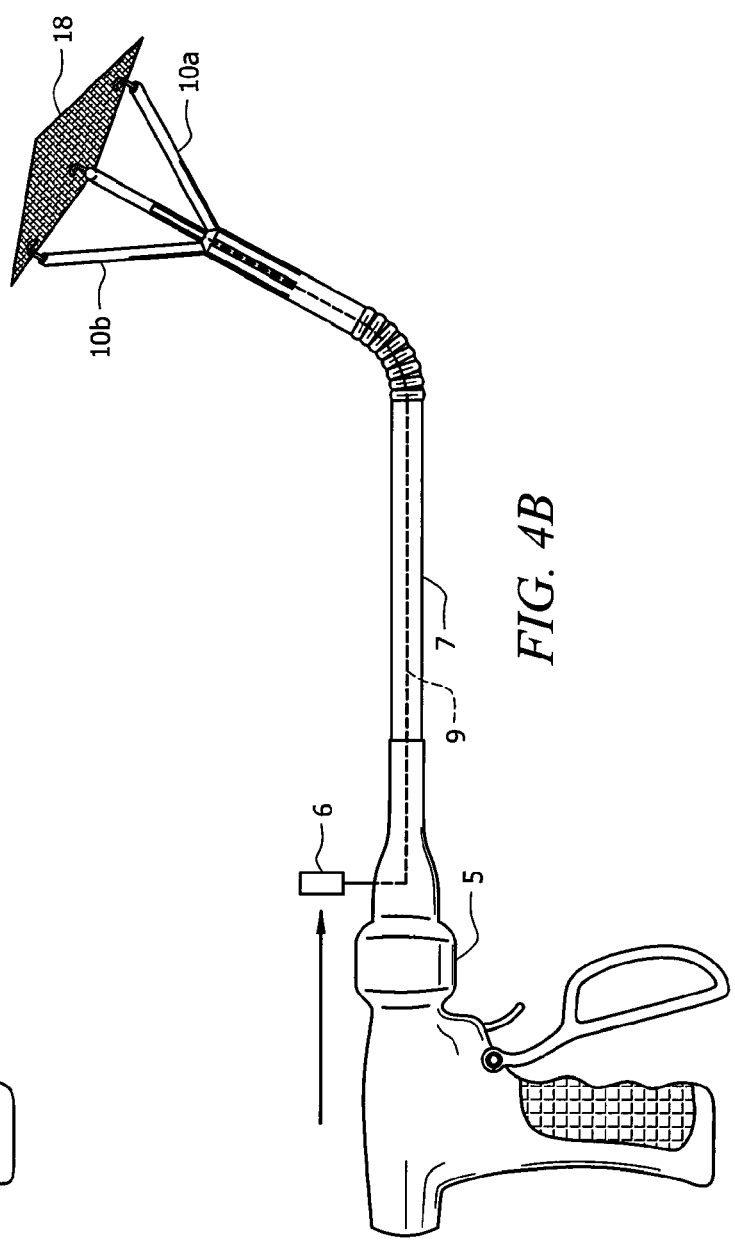
FIG. 4A
FIG. 4B

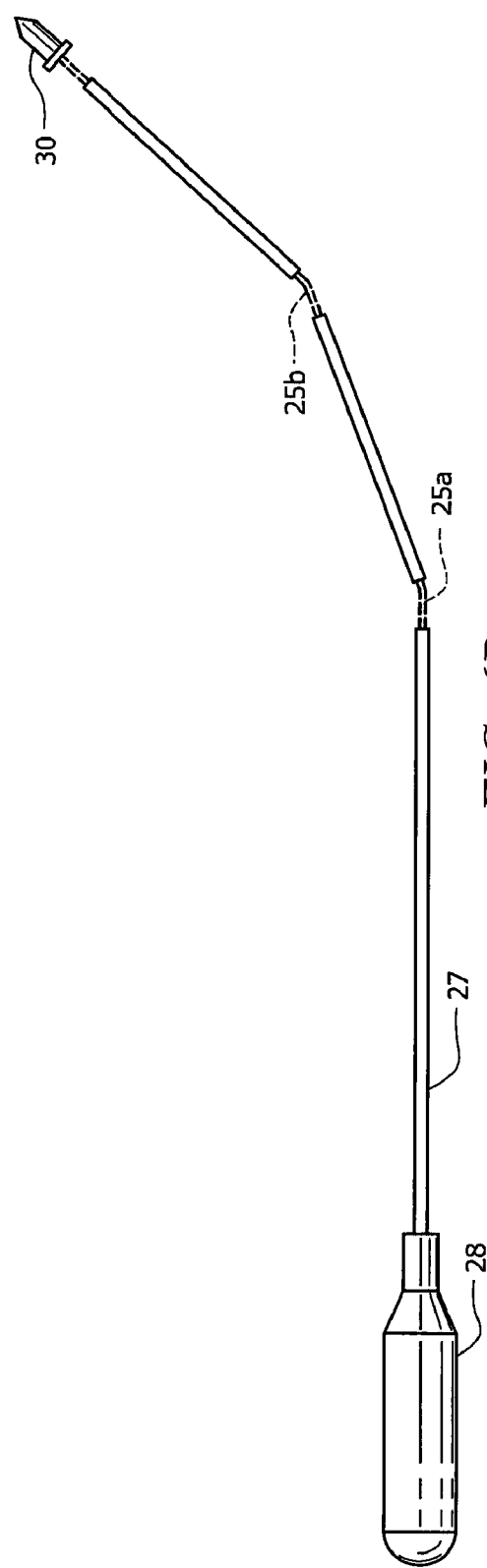
FIG. 6A
FIG. 6B

LAPAROSCOPIC HERNIA MESH SPREADER

CROSS REFERENCE TO RELATED APPLICATIONS

This application is a continuation of prior filed International Application, Serial Number PCT/US2006/034958 filed Sep. 8, 2006, which claims priority to U.S. provisional patent application No. 60/596,233 filed Sep. 9, 2005 which is hereby incorporated by reference into this disclosure.

FIELD OF INVENTION

This invention relates to an apparatus and method for the laparoscopic deployment and positioning of surgical materials, such as mesh.

BACKGROUND OF THE INVENTION

Inguinal hernia repair is performed by two principal techniques: (1) open, requiring a large incision for repair of the disrupted tissue by suture or the placement of synthetic mesh in the abdomen; and (2) laparoscopic, using minimally invasive tools, inserted through ports placed through the skin, to position synthetic mesh in the abdominal cavity. Traditionally laparoscopic hernia repair is performed through three ports; one port for the camera by which the surgeon visualizes the operation, and two ports for the instruments used to place the mesh against the abdominal wall. Inserting the mesh into the abdomen is generally done by rolling the mesh around an instrument with jaws that can hold the mesh and then pushing it through a port, after which the surgeon uses two instruments to unroll the mesh, and staple it to the abdominal wall.

U.S. Pat. No. 5,304,187, for example, teaches an apparatus wherein the surgical mesh is wrapped around a tubular sleeve and then extruded in an unwinding motion. The device also employs manipulating jaws at its distal-most end which are used to manipulate the unwound mesh into position. Maneuvering of the mesh, however, is generally arduous, because the mesh tends to roll up on itself and has little rigidity.

Another mesh applicator for laparoscopic hernia repair is disclosed in U.S. Pat. No. 5,383,477. The device of the '477 patent employs pivotally extension arms for spreading a section of surgical mesh and holding it in place for subsequent attachment. To attach the mesh, however, a second affixing mechanism (i.e. surgical stapler) must be inserted into the abdomen while the spreader is deployed. This requires the use of an additional incision, which can lead to complications.

Therefore, what is needed is a device for efficiently deploying a surgical mesh, such as mesh, inside a body cavity while minimizing the number of incisions and surgical devices required.

SUMMARY OF INVENTION

In an illustrative embodiment, the invention includes a device for surgically treating hernia. The device includes a shaft having a distal end and a proximal end, relative to a user, with a central aperture through the longitudinal axis of the shaft; a primary rod is adapted for slidable movement within the central aperture of the shaft. At least one extension arm at the distal end of the primary rod is adapted for movement between a retracted position and an extended position. The extension arm is in axial alignment with the shaft in the retracted position and at a divergent angle relative to the longitudinal axis of the shaft in the extended position. The arms are disposed to apply the surgical repair material, such as a mesh.

In a second embodiment, the device also includes an attaching mechanism at the end of the arm to secure the repair material to an abdominal wall. Examples of attaching mechanisms include surgical staplers, adhesive dispenser and/or a heating element.

In a third embodiment, the extension arm has a central aperture through the longitudinal axis thereof. An extension rod is adapted for slidable movement through the central aperture of the arm and the central aperture of the shaft. The movement of the extension rod urges the surgical material into direct contact with an abdominal wall.

In a fourth embodiment, the extension arm is at least partially disposed within the central aperture of the shaft in the retracted position such that the at least one arm is inwardly radially biased by the shaft. The extension arm extends from the distal end of the shaft responsive to the actuation of the primary rod such that it expands radially.

In a fifth embodiment, the device includes a flexible joint on the shaft. A joint filament is attached to the inside of the shaft at a point distal to the flexible joint. Movement of the proximal end of the filament urges the end of the shaft distal to the flexible joint into angular relation to the end of the shaft proximal to the flexible joint.

It yet another embodiment, the invention uses an extension arm at the distal end of the primary rod adapted for movement between a retracted position and an extended position. The extension arm is in axial alignment with the shaft in the retracted position and at a divergent angle relative to the longitudinal axis of the shaft in the extended position. A surgical repair material, such as a mesh having memory characteristics, is releasably attached to the extension arm. The extension arm is at least partially disposed within the shaft in the retracted position such that the extension arm is inwardly radially biased by the shaft. The extension arm extends from the distal end of the shaft responsive to the actuation of the rod such that the extension arm expands radially.

BRIEF DESCRIPTION OF THE DRAWINGS

For a fuller understanding of the invention, reference should be made to the following detailed description, taken in connection with the accompanying drawings, in which:

FIG. 1A is a semi-exploded view of an illustrative embodiment of the mesh spreader.

FIG. 1B is a perspective view of a single extending arm.

FIG. 1C is a perspective view of a plurality (4) extension arms deploying the surgical mesh.

FIG. 2A is a perspective view of the shaft having a flexible joint and rigid, hinged extension arms of one embodiment of the inventive mesh spreader; wherein the angled extension arms are in the retracted position and the shaft is substantially straight.

FIG. 2B is a perspective view of the shaft having a flexible joint and rigid, hinged extension arms of one embodiment of the inventive mesh spreader; wherein the angled extension arms are in the extended position and the shaft is substantially straight.

FIG. 3A is a perspective view of a shaft having a flexible joint; wherein the shaft is substantially straight.

FIG. 3B is a perspective view of a shaft having a flexible joint; wherein the shaft is disposed at an angle.

FIG. 4A is a perspective view of an embodiment having a shaft with a flexible joint, a primary rod and employing the use of resilient extension arms; retracted position.

FIG. 4B is a perspective view of an embodiment having a shaft with a flexible joint, a primary rod and employing the use of resilient extension arms; extended position.

FIG. 6A illustrates an exemplary attachment mechanism of the instant invention.

FIG. 6B illustrates the exemplary attachment mechanism of FIG. 6A in its extended state.

DETAILED DESCRIPTION OF THE PREFERRED EMBODIMENT

Figure 2C:
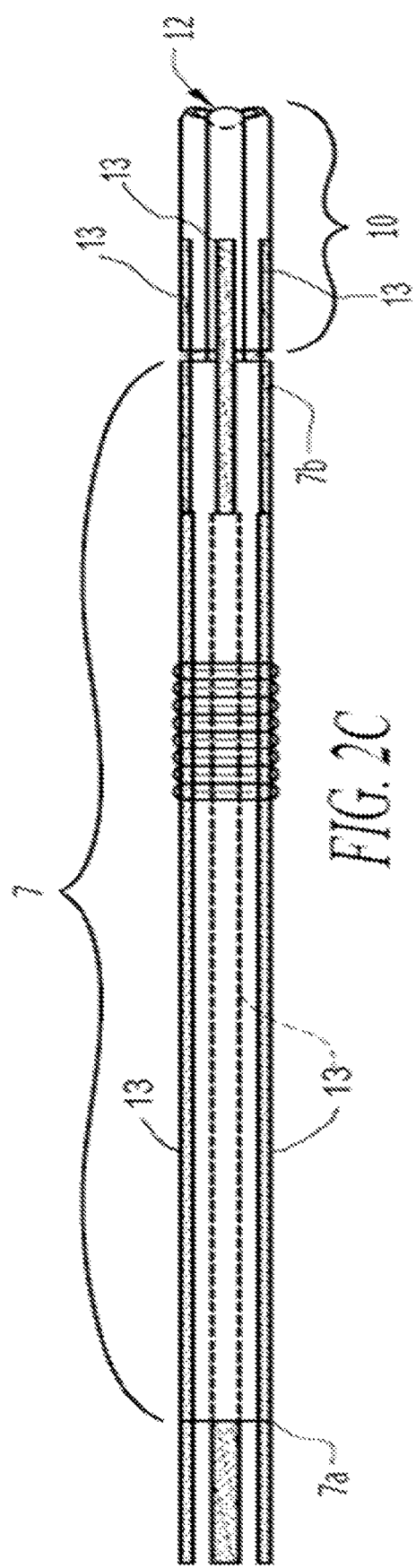
FIG. 2C is a perspective view of the shaft illustrating each extension arm having a corresponding extension rod therethrough which extends through the shaft to terminate at its own lever. The manipulation of the lever moves the corresponding extension rod. This embodiment has a flexible joint and rigid, hinged extension arms; wherein the angled extension arms are in the retracted position and the shaft is substantially straight.

In the following detailed description of the preferred embodiments, reference is made to the accompanying drawings, which form a part hereof, and within which are shown by way of illustration specific embodiments by which the invention may be practiced. It is to be understood that other embodiments may be utilized and changes may be made without departing from the scope of the invention.

FIG. 1A shows an illustrative embodiment of hernia mesh applicator 1. Generally, mesh applicator 1 includes handle 5, shaft 7 and a plurality of extension arms 10 (shown here in the retracted position). Shaft 7 further includes proximal end 7a and distal end 7b (relative to the user). Each arm (also having a proximal end 11 and distal end 12) has holding mechanism or connector 14 for releasably engaging the surgical mesh (FIG. 1B). FIG. 1C illustrates the position of the arms in the extended position with a section of repair mesh 18 attached to holding mechanisms or connectors 14 for positioning across a herniation.

The intra-abdominal portion of mesh spreader 1, comprising shaft 7 and extension arms 10, are dimensioned to be inserted through a surgical port or trochar to gain access to the patient's abdomen. For example, the diameter of shaft 7 in one embodiment is about 10-12 millimeter; standard laparoscopic dimensions. It is however possible to use larger diameter parts, but the use of larger parts requires the use of larger incisions.

After insertion of the intra-abdominal portion of mesh spreader 1, the user operates at least one lever or trigger on handle 5 causing extension arms 10 to move from the retracted position (FIG. 1A) to the extended position (FIG. 1C). Each extension arm 10 supports a corner of precut surgical mesh 18. Once surgical mesh 18 is in place, the user can activate the attaching mechanism to secure the material to the abdominal wall.

In use, the extension arms are connected to a piece of surgical mesh having a predetermined size and shape. The surgical mesh can be connected to the extension arms and loaded in the shaft during construction; or the user can select from various sizes of material and load the mesh spreader prior to use.

The following represent examples of alternate embodiments of the inventive mesh spreader; each constituting significant advantages over the prior art.

Example 1

Rigid Arm Mesh Spreader with Extension Arms Hingedly Connected

An embodiment employing a plurality of substantially rigid extension arms 10 is shown in FIGS. 1A through 1C and 2A through 2C. Here, a at least one substantially rigid rod 9 is mounted within shaft 7. Rod 9 is connected to a lever on handle 5 at its proximal end, and extension arms 10 at its distal end. Extension arms 10 are hingedly connected to the distal end of rod 9. The action of the hinges is preferably in a single, predetermined plane such as that of an elbow joint. This allows predictable deployment of the mesh when the extension arms 10 are activated.

Different styles and types of hinges may be used in conjunction with the present invention. For example, hollow cylindrical hinges that allow the passage of filaments 22 there through may be used in certain embodiments of the invention. It is also possible to use hinges of a round metal mesh or flexible tubular material. Although such a hinge is not limited to a single plane, the attachment of the surgical mesh to all extension arms 10 will limit their movement.

Activation of extension arms 10 can be achieved through manipulation of single rod 9 as depicted in FIG. 2A. However, it is also possible to use an independently moving extension rod 13 for each extending arm 10 as depicted in FIG. 2C. This would allow precise manipulation of surgical mesh 18 as it is deployed.

A measure of fine-tuning is provided through the placement of an extension rod 13 (FIG. 1B, 2C) in each extending arm 10. Each extension rod 13 extends through the distal end of extension arm 10, into and through shaft 7, and terminates in a lever on handle 5. (FIG. 2C) Each extension rod 13 may terminate in its own lever. The distal end of extension rod 13 is equipped with holding mechanism or connector 14 for releasably engaging surgical mesh 18. Manipulating the lever on handle 5 extends the corresponding extension rod 13 outward from the distal end of arm 10. It is possible to arrange the extension rods 13 to achieve independent or simultaneous contact between the corners of surgical mesh 18 and the abdominal wall. The tip of extension rod 13 is also equipped with the appropriate attaching mechanism, as discussed herein.

Example 2

Adjustable Shaft Mesh Spreader

In most embodiments, it is preferable that the distal ends of extension arms 10 angled at approximately 45 degrees (see FIGS. 2A and 2B) because the abdominal wall faces downward. Angling the distal ends of the extension arms allows all four arms 10 to be perpendicular, and in direct contact with, the abdominal wall when the extension arms are deployed.

Alternatively, flexible joint 20 at a point along the intra-abdominal section of shaft 7 also allows such placement. (FIGS. 2A, 2B, 3A, 3B, 4A, 4B, 5A and 5B) It is also important to note that the use of such a flexible joint 20 is not mutually exclusive with the use of angled extension arms 10.

Turning now to FIG. 3A, joint filament 22 is attached to the inside of shaft 7 at point 24, distal to flexible joint 20. Filament 22 is slidably disposed within shaft 7 at a point proximal to flexible joint 20 at point 24a which is preferably on the opposite side of fixed connection 24. The proximal end of filament 22 is connected to a control on handle 5 that allows adjustable manipulation thereof. As the force from the control on handle 5 is applied to filament 22 (and by virtue thereof to fixed connection point 24), shaft 7 forms a bend (as shown in FIG. 3B). The bend in flexible joint 20 places the distal end of the shaft at an angle relative to the proximal end; thereby placing the end of the instrument in proper alignment for attaching the mesh. Joint filament 22 can also be used in the embodiments of the invention shown in FIGS. 2A, 2B, 4A, 4B, 5A and 5B as indicated in the depiction of the flexible joint 20 in each of these figures.

Example 3

Flexible Arm Mesh Spreader

An alternative embodiment employs a plurality of resilient extension arms; in contrast to the rigid, hinged arms described previously. A single rod 9 can be used to extend and retract the extension arms 10. In other embodiments, each extending arm is actuated by its own lever.

Referring now to FIGS. 4A and 4B; extension arms 10 are made of a resilient material and have a retracted position (FIG. 4A) and extended position (FIG. 4B). In the retracted position of FIG. 4A, extension arms 10 are at least partially disposed within shaft 7. Moreover, the distal ends of extension arms 10 are inwardly radially biased by shaft 7 with the proximal ends co-joined at the distal end of rod 9.

In the extended position of FIG. 4B, extension arms 10 have been released from shaft 7 by the forward motion of lever 6 and thereby rod 9. Accordingly, extension arms 10 are no longer inwardly radially biased by shaft and expand as a result of their resiliency. Here, the expanded arms form a generally rectangular configuration; the upper extension arms 10a being spaced apart from lower extension arms 10b. The illustrative embodiment of FIG. 4B employs the use of relatively shorter upper extension arms 10a to create an angle for proper placement of surgical mesh 18. As previously discussed, alternate embodiments may instead employ a shaft (7) equipped with a flexible joint, or a shaft (7) having a permanent bend.

Example 4

Single Arm Mesh Spreader

Some commercially available forms of surgical mesh contain flexible frameworks with "memory" that spring into shape once inserted into the abdomen. Another embodiment of the current invention takes advantage of such devices to reduce the number of moving parts in the applicator; thereby increasing the ease of manufacture as well as removing points of potential failure.

Figure 5A:
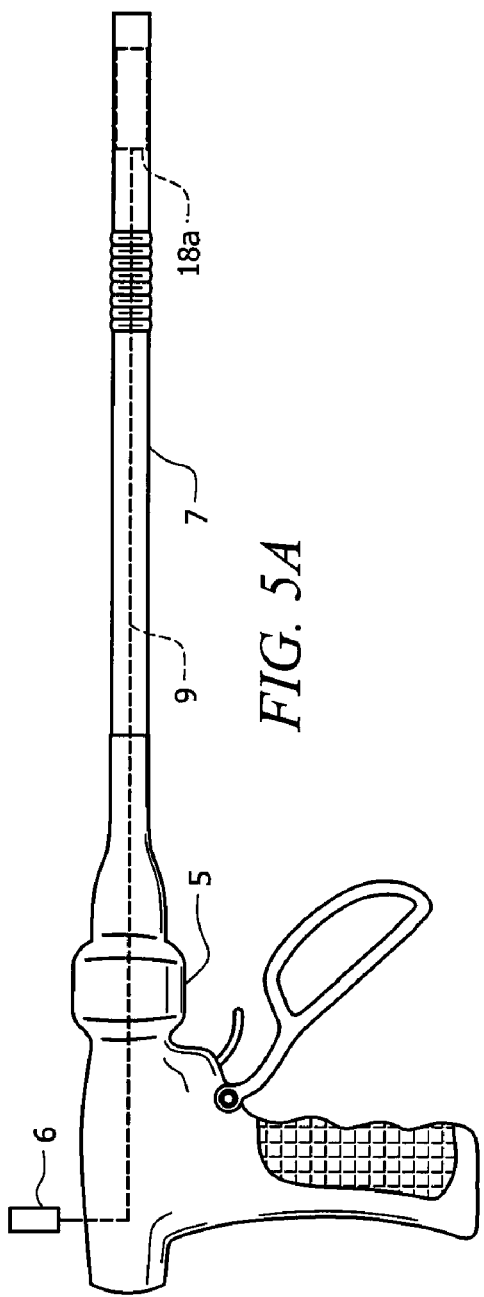
FIG. 5A is a perspective view of an embodiment having a shaft with a flexible joint and employing the use of a single resilient extension arm and a piece of "memory" mesh; retracted position.
Figure 5B:
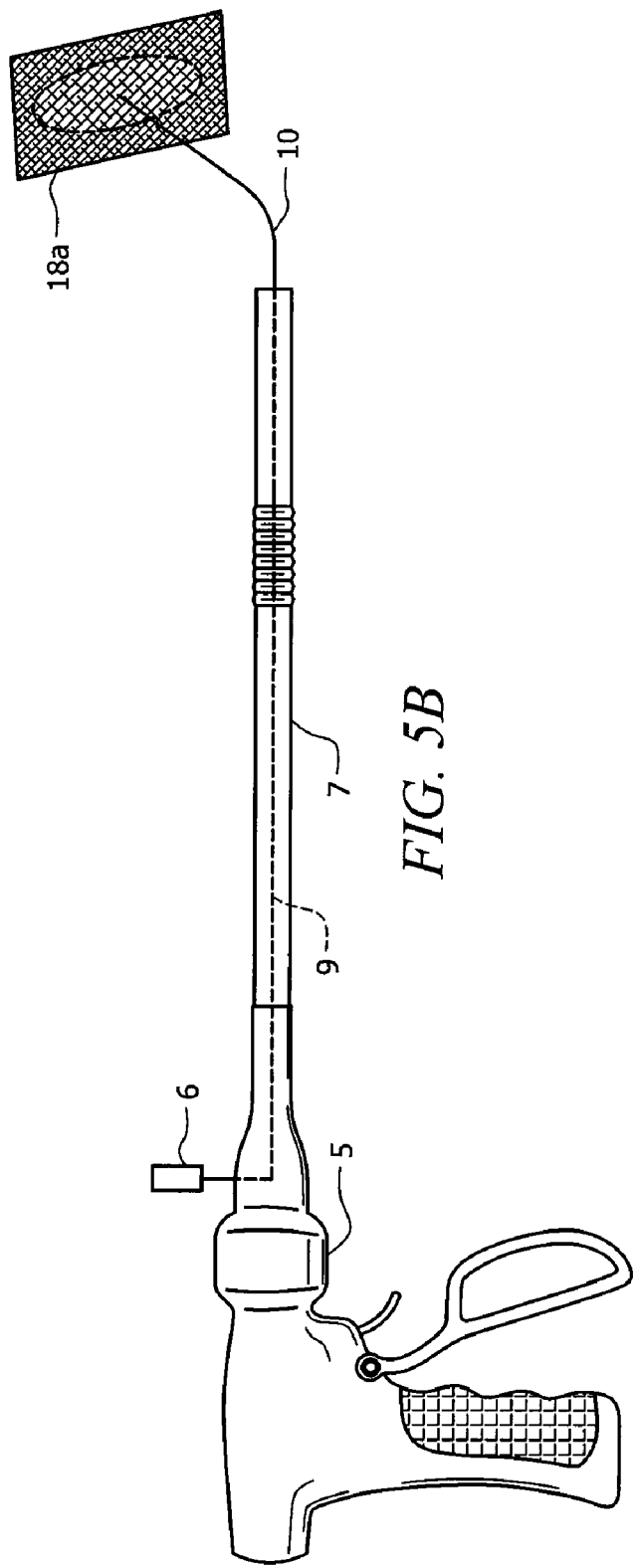
FIG. 5B is a perspective view of an embodiment having a shaft with a flexible joint and employing the use of a single resilient extension arm and a piece of "memory" mesh; extended position.

The embodiment of the invention shown in FIGS. 5A and 5B uses a single extension arm 10 as an extension of rod 9. The operation of the device is similar to those discussed above. Once distal end 7b of shaft 7 is placed adjacent the hernia to be repaired, the user pushes lever 6 forward to deploy the extension arm and surgical mesh.

Referring now to FIG. 5A, it can be seen that the plurality of arms in the previous embodiments have been replaced with a single arm 10. As with the previous embodiment; surgical mesh 18a can be loaded into the device at manufacture or prior to surgery by the user. Here the "memory" mesh 18a is wrapped into substantially cylindrical form and resides within shaft 7. The inner diameter of shaft 7 inwardly radially biases mesh 18a.

In FIG. 5B, lever 6 is actuated which urges extension arm 10, which is connected to surgical mesh 18a, from the distal end of shaft 7. Memory mesh 18a expands since it is no longer inwardly radially biased by shaft 7. In the embodiment shown in FIG. 5B, extension arm 10 is also comprised of a resilient material with "memory" characteristics.

As with the embodiment discussed previously, extending arm 10 has a retracted position (FIG. 5A) and extended position (FIG. 5B). In the retracted position of FIG. 5A, extending arm 10 is at least partially disposed within shaft 7. Moreover, the distal end of extending arm 10 is also inwardly radially biased by shaft 7 with the proximal end attached to the distal end of rod 9; such that they form in substantially linear configuration.

In the extended position of FIG. 5B, extending arm 10 has been released from shaft 7 by the forward motion of lever 6 and thereby rod 9. Accordingly, extending arm 10 and memory mesh 18a are no longer inwardly radially biased by shaft and expand as a result of their resiliency. Here, the expanded mesh 18a forms a generally rectangular configuration with extending arm 10 attached substantially in the middle thereof. The illustrative embodiment of FIGS. 5A and 5B employs the use of a resilient extending arm 10a to create the angle for proper placement of memory mesh 18a. As previously discussed, alternate embodiments may instead employ a shaft (7) equipped with a flexible joint, or a shaft (7) having a permanent bend.

Example 5

Attaching Mechanisms

The attaching mechanism can take many forms. For example, the distal ends of the extension arms can be equipped with pneumatic or spring-loaded surgical staplers or nailers; a dispenser of low-viscosity glue, such as those already used for surgical wound-closure; and/or heating elements that use electrical current to active a heat-activated adhesive on the surgical mesh. Such electro-cauterization techniques are available since the patient is normally grounded. The use of substantially cylindrical arms in some embodiments provides the structural support and room needed to accommodate some attaching mechanisms. Moreover, the need for additional ports is avoided because of the incorporation of such attachment mechanisms to the spreading device.

Once the surgical mesh is attached, connectors 14 (FIG. 1B) disengage mesh 18. Surgical mesh 18 can then be further reinforced by staples or tacks, as are known. Various methods of releasing the surgical mesh are envisioned. The extension arms, for example, could have an area of decreased diameter at their distal ends. The mesh could likewise be adapted with holes of the same decreased diameter through which the extension arms could pass; the mesh resting in the notch created by the smaller diameter of the arms. Once secured, the user simply pulls the extension arms free of the mesh. In another embodiment, the extension arms could be made of a conductive material whereby application of a low current would melt the surgical mesh proximate to the extension arms; thereby releasing the mesh. In yet another embodiment, connectors 14 (FIG. 1B) could be constructed from a material capable of being severed by a surgical instrument, such as scissors or a scalpel.

An illustrative embodiment incorporating an illustrative attaching mechanism is shown in FIGS. 6A and 6B. In this embodiment, a cable or linkage of cables and/or metal rods transmit a force sufficient to embed surgical tack 30 into the abdomen wall. In a preferred embodiment, this particular attaching mechanism is used in conjunction with the rigid arm mesh spreader described above.

Turning to FIG. 6A, cable 27 of the attaching mechanism is a substantially rigid and hollow tube. This configuration allows cable 27 to transmit the force generated by a pressurized fluid (such as $CO_2$) 28. Cable 27 must be sufficiently rigid to prevent the cable from doubling up on itself when the force is applied. This ensures that the greatest amount of force is transferred to surgical tack 30.

Flexible tube 25a can be placed inside cable 27 for embodiments which employ a flexible joint or bent shaft. Flexible tube 25a provides the necessary flexibility to accommodate the dynamic action of the flexible joint embodiments. FIG. 67B is illustrative of such an embodiment wherein the flexible joint has been actuated (25a) and the relevant extension arm is deployed (25b).

Although the device has been presented for the treatment of inguinal hernia repair, other uses are also contemplated. For example, an incisional hernia is an area where the abdominal wall has a structural defect due to previous surgery, allowing the abdominal contents to herniate. For the laparoscopic repair of incisional hernias that are located away from the patient's midline, the device could be used in the same manner as with inguinal hernias. However, these hernias are commonly located in the center of the abdominal wall which makes application of the mesh even more difficult as the abdominal wall is facing downward, forcing the surgeon to operate with the instruments at awkward angles. For incisional hernias of the abdominal wall midline, the mesh-deployment device could be inserted through the site of the hernia and the mesh, when spread, would then cover the defect without significant maneuvering as the mesh would already be at the site of the defect.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A device, comprising:
a shaft having a distal end and a proximal end, relative to a user, and having a central aperture through the longitudinal axis of the shaft;
a flexible joint on the shaft;
a joint filament, having a distal end and a proximal end, attached to the inside of the shaft at a point distal to the flexible joint;
whereby movement of the proximal end of the filament urges the end of the shaft distal to the flexible joint into angular relation to the end of the shaft proximal to the flexible joint;
a primary rod having a distal end and a proximal end, relative to the user, adapted for slideable movement within the central aperture of the shaft;
at least one arm at the distal end of the primary rod adapted for movement between a retracted position and an extended position;
wherein the at least one arm is in axial alignment with the shaft in the retracted position and the at least one extension arm is at a divergent angle relative to the longitudinal axis of the shaft in the extended position;
a surgical repair material releasably attached to the at least one arm; and
an attaching mechanism at the end of the at least one arm adapted to secure the repair material to an abdominal wall.

2. The device of claim 1 further comprising a plurality of arms that vary in length.

3. The device of claim 1 wherein the distal end of the at least one arm is angled to provide direct contact with the abdominal wall in the extended position.

4. The device of claim 1 further comprising a holding mechanism at the distal end of the at least one arm adapted to apply the surgical material.

5. The device of claim 1 wherein the at least one arm has a central aperture through the longitudinal axis thereof; and further comprising an extension rod, having a proximal end and a distal end, adapted for slideable movement through the central aperture of the at least one arm and the central aperture of the shaft;
wherein the movement of the extension rod urges the surgical material into direct contact with the abdominal wall.

6. The device of claim 1 wherein the at least one arm is at least partially disposed within the central aperture of the shaft in the retracted position such that the at least one arm is inwardly radially biased by the shaft; and
wherein the at least one arm extends from the distal end of the shaft responsive to the actuation of the primary rod such that the at least one arm expands radially.

7. A device, comprising:
a shaft having a distal end and a proximal end, relative to a user, and having a central aperture through the longitudinal axis of the shaft;
a flexible joint located on the shaft;
a joint filament, having a distal end and a proximal end, attached to the inside of the shaft at a point distal to the flexible joint;
whereby movement of the proximal end of the filament urges the end of the shaft distal to the flexible joint into angular relation to the end of the shaft proximal to the flexible joint;
a primary rod having a distal end and a proximal end, relative to the user, adapted for slideable movement within the central aperture of the shaft;
a plurality of arms at the distal end of the primary rod adapted for movement between a retracted position and an extended position;
wherein the plurality of arms are in axial alignment with the shaft in the retracted position and the plurality of arms are at a divergent angle relative to the longitudinal axis of the shaft in the extended position;
a surgical repair material releasably attached to the plurality of arms; and
wherein the plurality of arms have a central aperture through the longitudinal axis thereof; and further comprising an extension rod, having a proximal end and a distal end, adapted for slideable movement through the central aperture of each of the plurality of arms and the central aperture of the shaft;

wherein the movement of the extension rod urges the surgical material into direct contact with an abdominal wall.

8. The device of claim 7 further comprising the plurality of arms varying in length.

9. The device of claim 7 wherein the distal ends of the plurality of arms are angled to provide direct contact with the abdominal wall in the extended position.

10. The device of claim 7 further comprising a holding mechanism at the distal ends of the plurality of arms adapted to apply the surgical material.

11. The device of claim 7, further comprising an attaching mechanism at the end of at least one arm adapted to secure the repair material to the abdominal wall.

12. The device of claim 7 wherein the plurality of arms are at least partially disposed within the central aperture of the shaft in the retracted position such that the plurality of arms are inwardly radially biased by the shaft; and wherein the plurality of arms extend from the distal end of the shaft responsive to the actuation of the primary rod such that the plurality of arms expand radially.

13. A device, comprising:
a shaft having a distal end and a proximal end, relative to a user, and having a central aperture through the longitudinal axis of the shaft;
a flexible joint on the shaft;
a joint filament, having a distal end and a proximal end, attached to the inside of the shaft at a point distal to the flexible joint;
whereby movement of the proximal end of the filament urges the end of the shaft distal to the flexible joint into angular relation to the end of the shaft proximal to the flexible joint;
a primary rod having a distal end and a proximal end, relative to the user, adapted for slideable movement within the central aperture of the shaft;
at least one arm at the distal end of the primary rod adapted for movement between a retracted position and an extended position;
wherein the at least one arm is in axial alignment with the shaft in the retracted position and the at least one extension arm is at a divergent angle relative to the longitudinal axis of the shaft in the extended position;
a surgical repair material releasably attached to the at least one arm; and
wherein the at least one arm is at least partially disposed within the central aperture of the shaft in the retracted position such that the at least one arm is inwardly radially biased by the shaft; and
wherein the at least one arm extends from the distal end of the shaft responsive to the actuation of the primary rod such that the at least one arm expands radially.

14. The device of claim 13 further comprising a plurality of arms that vary in length.

15. The device of claim 13 wherein the distal end of the at least one arm is angled to provide direct contact with the abdominal wall in the extended position.

16. The device of claim 13 further comprising a holding mechanism at the distal end of the at least one arm adapted to apply the surgical material.

17. The device of claim 13 wherein the at least one arm has a central aperture through the longitudinal axis thereof; and further comprising an extension rod, having a proximal end and a distal end, adapted for slideable movement through the central aperture of the at least one arm and the central aperture of the shaft;

wherein the movement of the extension rod urges the surgical material into direct contact with the abdominal wall.

18. The device of claim 13, further comprising an attaching mechanism at the end of the at least one arm adapted to secure the repair material to the abdominal wall.

19. A device, comprising:
a shaft having a distal end and a proximal end, relative to a user, and having a central aperture through the longitudinal axis of the shaft;
a primary rod having a distal end and a proximal end, relative to the user, adapted for slideable movement within the central aperture of the shaft;
at least one arm at the distal end of the primary rod adapted for movement between a retracted position and an extended position;
wherein the at least one arm is in axial alignment with the shaft in the retracted position and the at least one extension arm is at a divergent angle relative to the longitudinal axis of the shaft in the extended position;
a surgical repair material releasably attached to the at least one arm; and
a flexible joint on the shaft; and
a joint filament, having a distal end and a proximal end, attached to the inside of the shaft at a point distal to the flexible joint;
whereby movement of the proximal end of the filament urges the end of the shaft distal to the flexible joint into angular relation to the end of the shaft proximal to the flexible joint.

20. The device of claim 19 further comprising a plurality of arms that vary in length.

21. The device of claim 19 wherein the distal end of the at least one arm is angled to provide direct contact with the abdominal wall in the extended position.

22. The device of claim 19 further comprising a holding mechanism at the distal end of the at least one arm adapted to apply the surgical material.

23. The device of claim 19 wherein the at least one arm has a central aperture through the longitudinal axis thereof; and further comprising an extension rod, having a proximal end and a distal end, adapted for slideable movement through the central aperture of the at least one arm and the central aperture of the shaft;

wherein the movement of the extension rod urges the surgical material into direct contact with the abdominal wall.

24. The device of claim 19, further comprising an attaching mechanism at the end of the at least one arm adapted to secure the repair material to the abdominal wall.

25. The device of claim 19 wherein the at least one arm is at least partially disposed within the shaft in the retracted position such that the at least one arm is inwardly radially biased by the shaft; and wherein the at least one arm extends from the distal end of the shaft responsive to the actuation of the rod such that the at least one arm expands radially.

26. A device, comprising:
a shaft having a distal end and a proximal end, relative to a user, and having a central aperture through the longitudinal axis of the shaft;
a flexible joint on the shaft;

a joint filament, having a distal end and a proximal end, attached to the inside of the shaft at a point distal to the flexible joint;

whereby movement of the proximal end of the filament urges the end of the shaft distal to the flexible joint into angular relation to the end of the shaft proximal to the flexible joint;

a primary rod having a distal end and a proximal end, relative to the user, adapted for slideable movement within the central aperture of the shaft;

an extension arm at the distal end of the primary rod adapted for movement between a retracted position and an extended position;

wherein the extension arm is in axial alignment with the shaft in the retracted position and at a divergent angle relative to the longitudinal axis of the shaft in the extended position;

a surgical repair material releasably attached to the extension arm; and wherein the extension arm is at least partially disposed within the shaft in the retracted position such that the extension arm is inwardly radially biased by the shaft; and wherein the extension arm extends from the distal end of the shaft responsive to the actuation of the rod such that the extension arm expands radially.

27. The device of claim 26 wherein the distal end of the extension arm is angled to provide direct contact with the abdominal wall in the extended position.

28. The device of claim 26 further comprising a holding mechanism at the distal end of the extension arm adapted to apply the surgical material.

29. The device of claim 26 wherein the extension arm has a central aperture through the longitudinal axis thereof; and further comprising an extension rod, having a proximal end and a distal end, adapted for slideable movement through the central aperture of the extension arm and the central aperture of the shaft;

wherein the movement of the extension rod urges the surgical material into direct contact with the abdominal wall.

30. The device of claim 26, further comprising an attaching mechanism at the end of the extension arm adapted to secure the repair material to the abdominal wall.

* * * * *